United States Patent [19]

Tyner

[11] Patent Number: 5,573,516
[45] Date of Patent: Nov. 12, 1996

[54] NEEDLELESS CONNECTOR

[75] Inventor: Clifford A. Tyner, Grass Valley, Calif.

[73] Assignee: Medical Connexions, Inc., San Rafael, Calif.

[21] Appl. No.: 529,929

[22] Filed: Sep. 18, 1995

[51] Int. Cl.⁶ .................................................. A61M 5/00
[52] U.S. Cl. ........................ 604/249; 604/256; 137/843
[58] Field of Search .................................. 604/283, 249, 604/280, 905, 256, 30–34; 137/851–854, 843

[56] References Cited

U.S. PATENT DOCUMENTS

| 4,324,239 | 4/1982 | Gordon et al. | 604/249 X |
|---|---|---|---|
| 4,429,856 | 2/1984 | Jackson | 604/283 |
| 4,842,591 | 6/1989 | Luther | 604/905 X |
| 5,163,922 | 11/1992 | McElveen, Jr. et al. | 251/149.1 |
| 5,215,538 | 6/1993 | Larkin | 604/283 X |
| 5,242,393 | 9/1993 | Brimball et al. | 604/283 |
| 5,242,423 | 9/1993 | Goodsir et al. | 604/283 X |
| 5,353,837 | 10/1994 | Faust | 604/905 |
| 5,360,413 | 11/1994 | Leason et al. | 604/249 |
| 5,395,348 | 3/1995 | Ryan | 604/247 |

Primary Examiner—John D. Yasko
Attorney, Agent, or Firm—Townsend and Townsend and Crew LLP

[57] ABSTRACT

A needleless connector includes a two-part housing with an inlet, an outlet, and a conical chamber therebetween that compressibly receives a resilient conical valve head. The conical valve head includes a stationary base, and a tip portion movably extending into the inlet. The conical valve head is concentrically positioned against the valve seat to form a seal. When the male fitting of a syringe, or some other device, is inserted into the inlet, it pushes a tip portion of the resilient valve head inwardly, so that the valve head is deformed away from the valve seat to break the seal. The needleless connector employs only three separate parts—the two-part housing, and the valve head—so that it is very economical to manufacture.

10 Claims, 3 Drawing Sheets

NEEDLELESS CONNECTOR

BACKGROUND OF THE INVENTION

1. Field of the Invention

This invention relates generally to fluid line or injection port connectors in medical applications, and specifically to a needleless connector having a novel valve construction.

2. Prior Art

Fluid connections in medical applications have been typically made by inserting a needle into an injection port on the end of a tube. A common use of needle connections is in intravenous fluid lines. However, the use of needles in making fluid connections contributes to the hundreds of thousands of accidental needle sticks in health care professionals each year. The possibility of contracting infections from such needle sticks is a serious and deadly risk.

Although needles cannot be eliminated from the health care industry, their use can be reduced. One particular area in which they can be minimized or eliminated is fluid connections. Accordingly, various needleless connectors have been proposed or offered. U.S. Pat. No. 5,163,922 to McElveen, Jr. et al. (1992) shows a needleless connector with an elastomeric, conical valve head (32) biased against a conical valve seat (30) by a helical spring (38) to form a seal. The entire valve head is movable and non-compressible. When the male fitting (50) of a syringe, after having the needle removed, pushes against an elongated tip of the valve head, the valve head is pushed away from the valve seat to allow the passage of fluid.

U.S. Pat. No. 4,915,687 to Sivert (1990) shows a needleless connector with a resilient biasing member (40) for biasing a valve head (50) against a valve seat (23). The entire valve head is movable and non-compressible.

U.S. Pat. No. 4,683,916 to Raines (1987) shows a needleless connector having a valve head (50) in the form of a resilient disc preloaded against a valve seat. The center of the disc is fixed in position. A separate, elongated tip or plunger (60) distorts the disc by pushing the rim thereof away from the valve seat to allow fluid flow.

U.S. Pat. No. 5,280,876 to Atkins (1994) shows a quick disconnect for medical instruments. It uses a resilient, tubular sleeve (23) that coaxially surrounds a tubular stem (19). A side port (21) on the stem is unsealed when the sleeve is distorted by a male connector.

Known needleless connector devices such as those described above, suffer from a number of disadvantages. Many employ separate valve heads and biasing members, and some employ a tip or plunger separate from the valve head. Together with two-part housings, such known needleless connector devices use at least four separate parts. Because needleless connectors are disposable, their cost is of great importance. Having at least four separate parts result in a connector which is relatively expensive. In addition, some are relatively complicated, so that they are not really intended for disposable applications. For example, the same needleless connector devices have a port is orthogonal to axis of the tubular stem, so that it cannot be easily injection molded.

Certain of the known needleless connectors use a valve mechanism that incorporates an elongate cylindrical member that, when compressed to deformation, opens to permit fluid flow. A problem with this type of valve mechanism is that while open, the cylindrical (or like) member opposes the compressive force to keep it open. This opposing force can tend to cause luer slip connections to separate—particularly if only a friction connection is used.

Accordingly it can be seen that there is needed an needleless connector capable of ameliorating, if not overcoming, the disadvantages attendant with known needleless connectors.

SUMMARY OF THE INVENTION

The present invention, therefore, provides a needleless connector that is inexpensive, simple to construct, and which poses no needle stick hazard to users, which can also be used as a check valve, and which employs a minimal number of separate parts for the greatest economy of manufacture.

According to an embodiment of the invention, there is provide a needleless connector formed from a two-part housing with an inlet, an outlet, and a conical chamber therebetween. A resilient, conical valve head received in the chamber is structured to be biased against an annular valve seat formed around the inner end of the inlet to form a fluid-tight seal. When a male fitting, such as that on a syringe, is inserted into the inlet, it pushes against an extension of the valve head, causing it to distort and be moved away from the valve seat to allow the passage of a fluid from the syringe. The valve head serves as both the seal and the biasing member, so that the present needleless connector has a total of only three separate parts, which is a parts reduction of at least 25% from prior art connectors. This translates into significant cost savings.

The conical valve head configured, when compressed for opening, to collapse onto itself in a way that provides a snap-action effect. The compressive force required to initially open the valve and permit fluid flow is higher than that is required to keep it open. Thus, once opened, the fluid flow may be maintained with less force than was required to establish the flow. This feature of the invention operates to minimize disconnection between the connecting parts used to open the valve.

Another advantage of the present invention is that the conical configuration of the valve head provides less volume for entrainment of fluids or solutions than the conical valve shapes used in some known needleless connectors that incorporate long, barrel-shaped valve structures. The conical configuration of the valve head also permits the construction of a needleless connector smaller than heretofore known.

These and other features and advantage of the present invention will become apparent to those skilled in this art upon a reading of the following detailed description of the invention which should be taken in conjunction with the accompanying drawings.

DESCRIPTION OF THE PREFERRED EMBODIMENT

Figure 1:
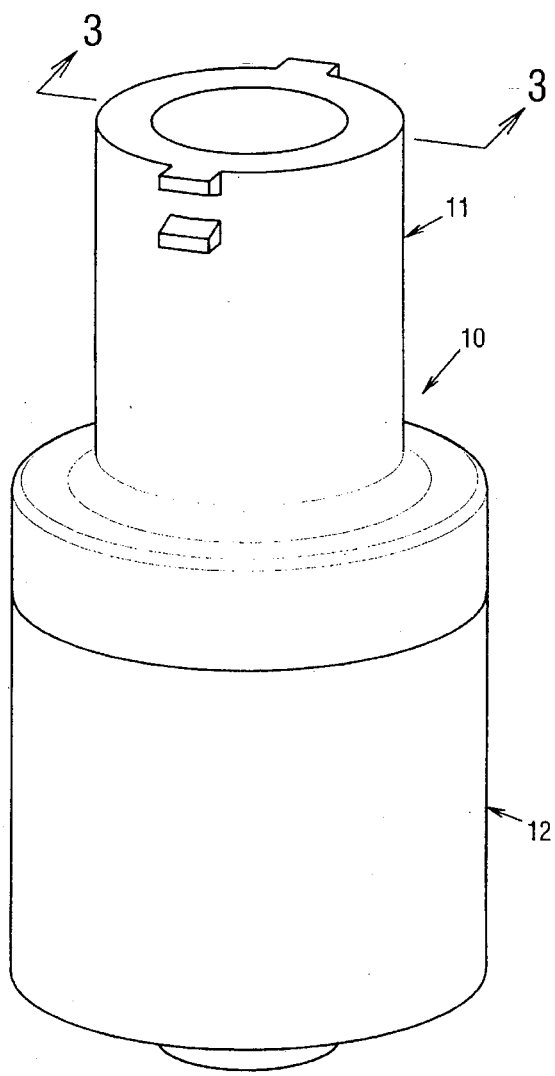
FIG. 1 is a perspective view of a needleless connector constructed in accordance with the teachings of the invention.
Figure 2:
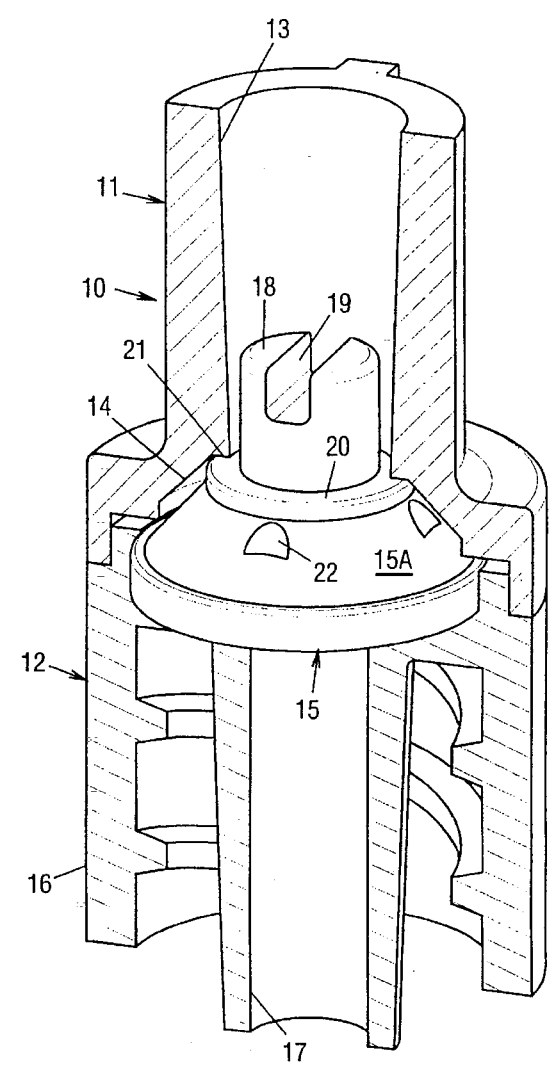
FIG. 2 is a front perspective, partial cutaway view of the needleless connector of FIG. 1.

Turning now to the Figures, the invention is shown in the front perspective view in FIG. 1, showing the needleless connector as including a housing 10 formed by first and second housing halves 11 and 12, respectively. The first housing half 11, shown in a cutaway view in FIG. 2, forms a female luer that includes a tapered, tubular fluid inlet 13, and a conical inner end 14 that receives a resilient, conical valve head 15 (shown whole). The second housing half 12 includes a conventional luer lock 16 for connecting to various types of medical fluid lines (not shown), and a tubular fluid outlet 17.

The valve head 15, as the figures show, is formed to be and conical in shape for reasons that will become apparent below. The upper portion of the valve head 15 includes an integral, elongated central tip portion 18, an annular base 25, and a thin-walled, conical wall 15a extending between the tip portion 18 and the base 25. The tip portion 18 has a smaller diameter than inlet 13 so that it can extend partially thereinto, and a transverse slot 19 on its distal end. The valve head 15 constructed to that when mounted in the chamber 14, the shoulder 20 is biased against an annular valve seat 21 around the inner end of inlet 13. Four radially-arranged fluid passages or apertures 22 (two shown) are formed in the web 17 of the valve head 15.

Preferably, the valve head 15 is constructed a thermoplastic rubber, such as "Sanopreme," available from Advanced Elastomer Systems of Akron, Ohio. (Sanopreme is a trademark of Monsanto Corporation.) A more expensive alternative is a thermoset rubber, such as a silicon rubber which is believed to have a better memory than thermoplastic rubber, allowing it to return to an original shape after long-term deformation.

Figure 3:
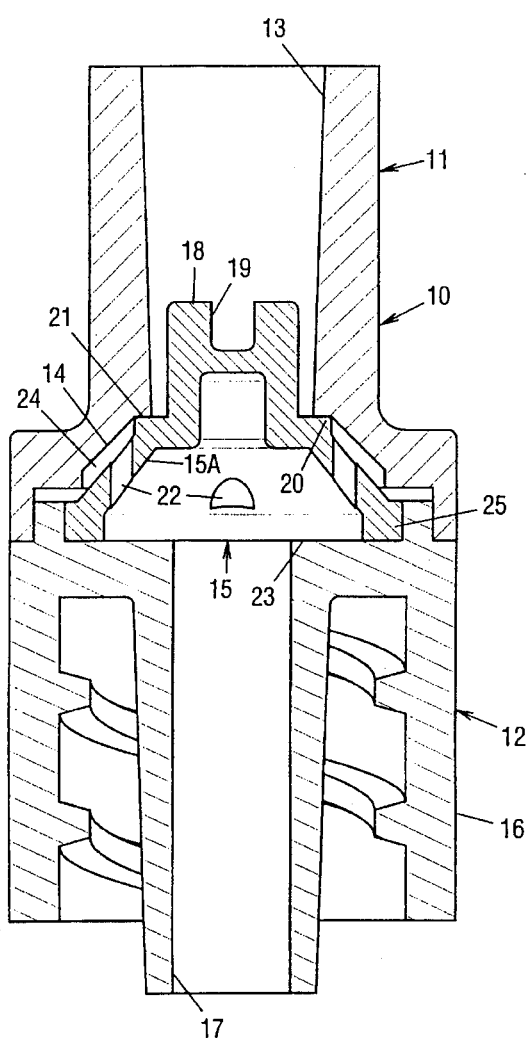
FIG. 3 is a side sectional view of the needleless connector, taken along line 3—3 in FIG. 1, in a closed condition.

As shown in the side sectional view in FIG. 3, conical inner end 14 of first housing half 11 and a flat inner end 23 of second housing half 12 cooperate to define a conical chamber 24. The conical wall 15a of the valve head 15 is made slightly taller than conical chamber 24 so that when valve head 15 is installed in chamber 24, the annular base 25 of valve head 15 will is tightly pressed against flat inner end 23, and shoulder 20 is biased against valve seat 21 to form a liquid-tight seal that closes access to the chamber 24 from the inlet 13. Any fluid in a fluid line (not shown) connected to luer lock 16 is kept from escaping out of inlet 13. The amount of compression or preload can be determined during manufacturing by varying the height of valve head 15 and its wall thickness. The conical portion of valve head 15 is spaced away from conical inner end 14.

The needleless connector of the present invention employs only three separate parts—first and second housing halves 11 and 12, and valve head 15. The nearest prior art connector employs at least four separate parts, so that the present connector achieves at least a 25% parts reduction.

Figure 4:
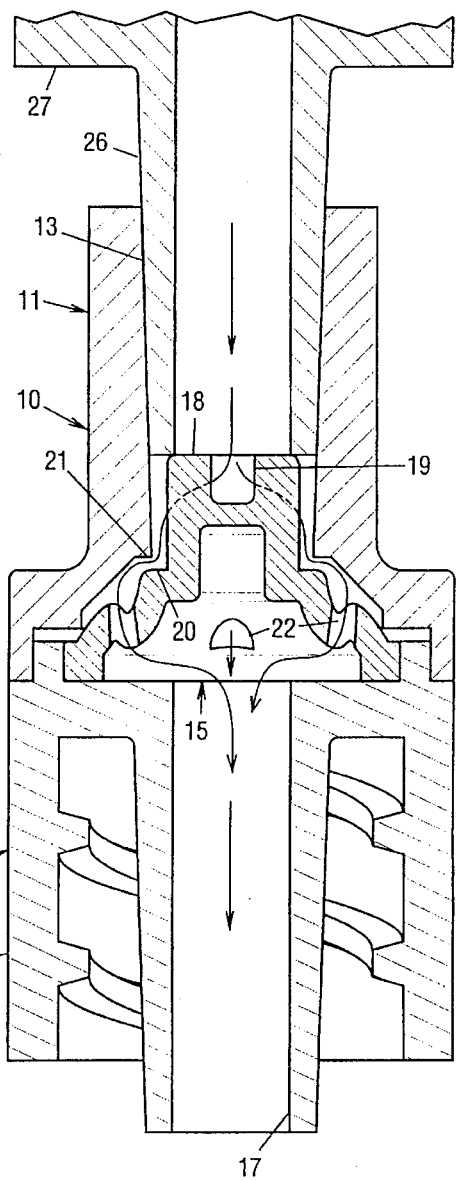
FIG. 4 is a side sectional view of the needleless connector in an opened condition.

When a standard male tubular fitting 26 of a needleless syringe 27, or any other fluid supply, is inserted into the inlet 13 far enough, the distal end of the fitting 26 will engage the tip portion 18 of the valve head 15. The tubular fitting 26 will exert a force, through the tip portion 18, on the conical portion of resilient valve head 15. When that force reaches sufficient magnitude, the conical portion of the valve head 15 deform, as shown in FIG. 4, collapsing onto itself so that the shoulder 20 is pushed away from valve seat 21. A path for fluid flow from the tubular fitting 26 is thereby created through and out the ends of slot 19, around the side of tip portion 18, through the gap now formed between the shoulder 20 and the valve seat 21, through apertures 22, and into outlet 17, as indicated by the arrows. When tubular fitting 26 is withdrawn from inlet 13 after injection, valve head 15 will rebound immediately to seal off inlet 13 and eliminate backflow. The present connector can be connected to any other medical device (not shown) having a standard male tubular fitting that is similar to fitting 26.

Figure 5:
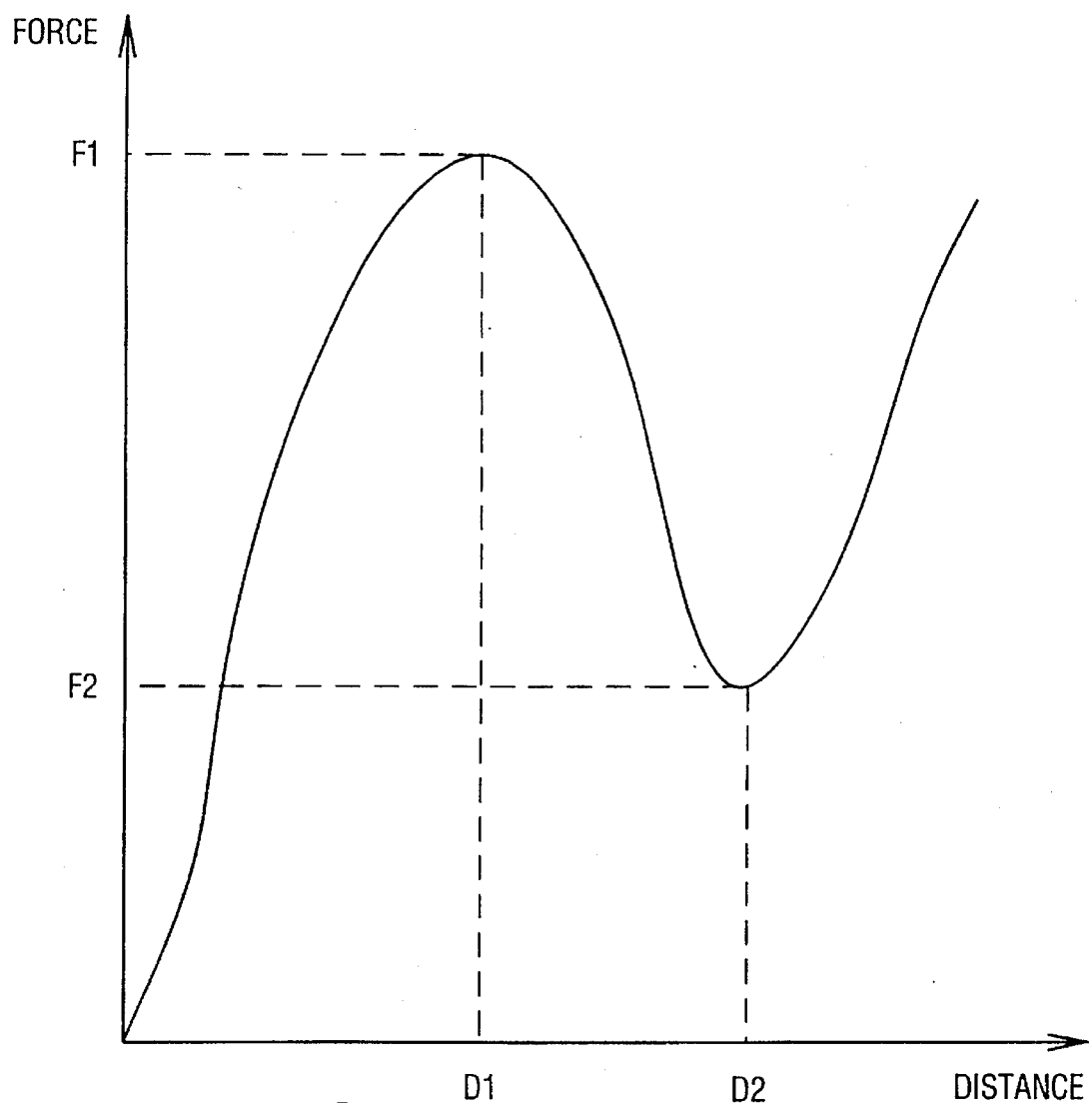
FIG. 5 is a graphical depiction of the force verses distance travelled, showing the snap-action effect provided by the present invention.

The walled structure of the conical portion of the valve head 15 causes it to operate as snap-action spring, requiring an initial, greater force to open the valve head (i.e., move the shoulder 20 away from the valve seat 21), than that to fully open the valve head (after the initial force is reached), and to maintain the valve head in an open condition. These forces are representatively illustrated in FIG. 5. FIG. 5 shows that when a force is imposed on the end portion 18, the valve head will begin to open, but only slightly. However, once a sufficient force of $F_1$ is reached, opening the valve head 15 so that the shoulder 20 is moved from the valve seat 21 a distance $D_1$, the conical portion of the valve head collapses, and the force needed to fully open the valve head 15, and to keep it open, drop to a force $F_2$, a force less than the force $F_1$. If the tubular fitting is to remain for some time, much less force is exerted against it by the valve head, minimizing inadvertent disconnection of the tubular member 26 from the housing half 10.

This snap-action capability of valve head 15 allows it to act as a relief valve. For example, if inlet 13 of the needleless connector is connected to a device or fluid line (not shown) without structure (such as the tubular member 26) to push against tip portion 18, valve head 15 will remain closed. The connector then will simply function as a one-way or check valve, i.e., valve head 15 will open if the pressure is greater on the side of inlet 13, but will close if the pressure is greater on the side of outlet 17.

Another feature of the valve head 15 that should now be apparent is the small volume created by the valve head 15 on the outlet side thereof for entrainment of fluids. Known connector apparatus using valve structures having elongate conical structures that, when compressed, open for fluid flow tent to entrain more fluid than desired when the valve closes.

Accordingly, the reader will see that the present invention provides an improved needleless connector connectable to a variety of medical fluid lines or devices without a needle, so that needle sticks are eliminated during its normal use. It can also function as a check valve. It employs only three separate parts, so that it is much more economical to manufacture than prior art needleless connectors.

Although the above descriptions are specific, they should not be considered as limitations on the scope of the invention, but only as examples of the preferred embodiment. Many other ramifications and variations are possible within the teachings of the invention. For example, the apertures on the valve head can be of a different shape, or may be replaced by forming apertures in the periphery or base 25 to permit fluid flow. The valve seat can be merely the rim of the inlet's inner end. The shoulder around the valve head can be eliminated, so that the valve head meets the valve seat with its conical side. The tip portion does not have to be elongated or extend into the inlet if the connector is only used as a check valve, i.e., the tip portion can simply be the central point of the conical valve head. Finally, although the invention has been described in an environment using luer lock fittments, it will be evident to those skilled in this art that various other fittments can be used with the invention.

What is claimed is:

1. A needleless connector, comprising:

a housing having a interior chamber, an inlet to the chamber, and an outlet from the chamber;

a valve seat formed in the chamber and proximate the inlet; and a resilient conical valve head mounted in the chamber, the valve head having a shoulder biased against the valve seat to form a fluid barrier between the inlet and the chamber, and an elongated tip portion positioned in the inlet having a transverse slot arranged thereon;

whereby a tubular fitting inserted into the inlet engages the tip portion to deform and collapse the conical valve head onto itself to move the shoulder away from the valve seat to permit fluid passage from the inlet, through the chamber, to the outlet.

2. The connector claim 1 wherein the inlet and the outlet are formed on the housing to be coaxially positioned at opposite ends of chamber.

3. The valve device of claim 1 wherein the conical valve head is hollow for allowing easy deformation.

4. The valve device of claim 1, wherein the shoulder is annularly configured and concentrically arranged around the conical valve head for engaging the valve seat.

5. The valve device of claim 1, further including a luer lock concentrically positioned around the outlet.

6. A needleless connector, comprising:

a housing formed to define an interior chamber, and having an inlet to the chamber and an outlet from the chamber;

a resilient conical valve head mounted in the chamber in a manner to close the chamber from the inlet, the conical valve head having a base and a movable tip portion pointing into the inlet, the tip portion being movable inwardly to deform the conical valve head away from the annular valve seat for breaking the seal, and an aperture extending through the conical valve head, whereby a tubular fitting inserted into the inlet engages the tip portion to deform the conical valve head to open the chamber to the inlet, so that a fluid fed from the tubular fitting can flow from the inlet, through the aperture, through the chamber to the outlet.

7. The valve device of claim 6 wherein the inlet and the outlet are coaxially positioned at opposite ends of the chamber.

8. The valve device of claim 6 wherein the conical valve head is hollow for allowing easy deformation.

9. The valve device of claim 6, further including an annular shoulder concentrically arranged around the conical valve head for engaging the annular valve seat.

10. The valve device of claim 6, further including a luer lock concentrically positioned around the outlet.

* * * * *